(12) United States Patent
Liu et al.

(10) Patent No.: US 12,213,940 B2
(45) Date of Patent: Feb. 4, 2025

(54) NEGATIVE-PRESSURE CUP STRUCTURE WITH LIGHT THERAPY MODULE

(71) Applicant: BIBOTING INTERNATIONAL CO., LTD., Taoyuan (TW)

(72) Inventors: Po-Chang Liu, Taoyuan (TW); Chia-Hsueh Hsieh, Taoyuan (TW); Pei-En Lee, New Taipei (TW)

(73) Assignee: BIBOTING INTERNATIONAL CO., LTD., Taoyuan (TW)

( * ) Notice: Subject to any disclaimer, the term of this patent is extended or adjusted under 35 U.S.C. 154(b) by 754 days.

(21) Appl. No.: 17/398,917

(22) Filed: Aug. 10, 2021

(65) Prior Publication Data
US 2023/0052405 A1 Feb. 16, 2023

(51) Int. Cl.
*A61N 5/06* (2006.01)
*A61H 9/00* (2006.01)
*A61M 1/08* (2006.01)

(52) U.S. Cl.
CPC ......... *A61H 9/0057* (2013.01); *A61N 5/0616* (2013.01); *A61H 2201/10* (2013.01); *A61M 1/08* (2013.01); *A61N 2005/0649* (2013.01); *A61N 2005/0652* (2013.01); *A61N 2005/0663* (2013.01); *A61N 2005/0666* (2013.01)

(58) Field of Classification Search
CPC .............. A61H 9/0057; A61H 2201/10; A61H 9/0007; A61H 9/00; A61H 9/005; A61N 5/0616; A61N 2005/0652; A61N 2005/0663; A61N 2005/0666; A61N 2005/0665; A61N 2005/0662; A61N 2005/0649; A61M 1/08
See application file for complete search history.

(56) References Cited

U.S. PATENT DOCUMENTS

| | | | |
|---|---|---|---|
| 2006/0039146 A1* | 2/2006 | Wu | F21V 23/04 362/235 |
| 2016/0175609 A1* | 6/2016 | Dye | A61N 5/0616 607/90 |
| 2020/0030627 A1* | 1/2020 | Eltorai | A61N 5/062 |

(Continued)

FOREIGN PATENT DOCUMENTS

| | | | | |
|---|---|---|---|---|
| CN | 105233421 A | * | 1/2016 | ............... A61N 5/06 |
| CN | 106823154 A | * | 6/2017 | |

(Continued)

OTHER PUBLICATIONS

CN 105233421 A Machine translation (Year: 2016).*

(Continued)

*Primary Examiner* — Timothy A Stanis
*Assistant Examiner* — Sara K Toich
(74) *Attorney, Agent, or Firm* — Chun-Ming Shih; HDLS IPR SERVICES

(57) ABSTRACT

A negative-pressure cup structure includes a negative-pressure cup body and a light therapy module. The negative-pressure cup body has a rim. The light therapy module is received in the negative-pressure cup body and includes a circuit board and multiple light-emitting diodes (LEDs) mounted on the circuit board and irradiating corresponding to the rim. Therefore, the negative-pressure cup structure further has functions of light therapy and skin care.

14 Claims, 9 Drawing Sheets

(56) References Cited

U.S. PATENT DOCUMENTS

2020/0179220 A1* 6/2020 Jablow .................... A61H 1/00
2023/0264039 A1* 8/2023 Liu ..................... A61N 5/0616
                                                          601/7

FOREIGN PATENT DOCUMENTS

CN        106860928 A  *  6/2017
KR      20140071875 A  *  6/2014  ........... A61H 9/0057

OTHER PUBLICATIONS

CN 106860928 A machine translation (Year: 2017).*
CN_106823154_A_I Machine translation (Year: 2017).*
KR_20140071875_A_I Machine translation (Year: 2014).*

* cited by examiner

NEGATIVE-PRESSURE CUP STRUCTURE WITH LIGHT THERAPY MODULE

BACKGROUND

Technical Field

The disclosure relates to a negative-pressure cup for medical therapy or healthcare, particularly to a negative-pressure cup structure with a light therapy module.

Related Art

A cup or a cupping cup used for covering a surface of human body utilizes negative pressure to stimulate skin, relax muscle or implement an effect of breast enhancement. Thus, that kind of cup or cupping cup becomes a healthcare gear widely appearing in the market.

However, in the related art, the cup or cupping cup merely relies on negative pressure to implement the therapeutic effect, so it has a problem of monotonous function. As a result, how to add functions to the cup or cupping cup is an issue to be solved by the industry.

In view of this, the inventors have devoted themselves to the above-mentioned related art, researched intensively and cooperated with the application of science to try to solve the above-mentioned problems. Finally, the invention which is reasonable and effective to overcome the above drawbacks is provided.

SUMMARY

The disclosure provides a negative-pressure cup structure with a light therapy module, which utilizes the light therapy module received in the negative-pressure cup body to make the negative-pressure cup structure have functions of light therapy and skin care.

In an embodiment of the disclosure, the disclosure provides a negative-pressure cup structure with a light therapy module, which includes a negative-pressure cup body and a light therapy module. The negative-pressure cup body has a rim. The light therapy module is received in the negative-pressure cup body and includes a circuit board and multiple light-emitting diodes (LEDs) mounted on the circuit board and irradiating corresponding to the rim.

Accordingly, the light therapy module further includes a condenser arranged corresponding to the LEDs. The condenser is provided with multiple via holes and multiple reflecting annular walls respectively formed in the multiple via holes. Each LED is arranged corresponding to the reflecting annular wall of each via hole. The reflecting annular wall possesses a great effect of reflection so as to make the lights from the LEDs be concentrated to irradiate out from the via holes. The light scattering may be avoided and the efficiency of light therapy of the negative-pressure cup structure may be enhanced.

DETAILED DESCRIPTION

Figure 1:
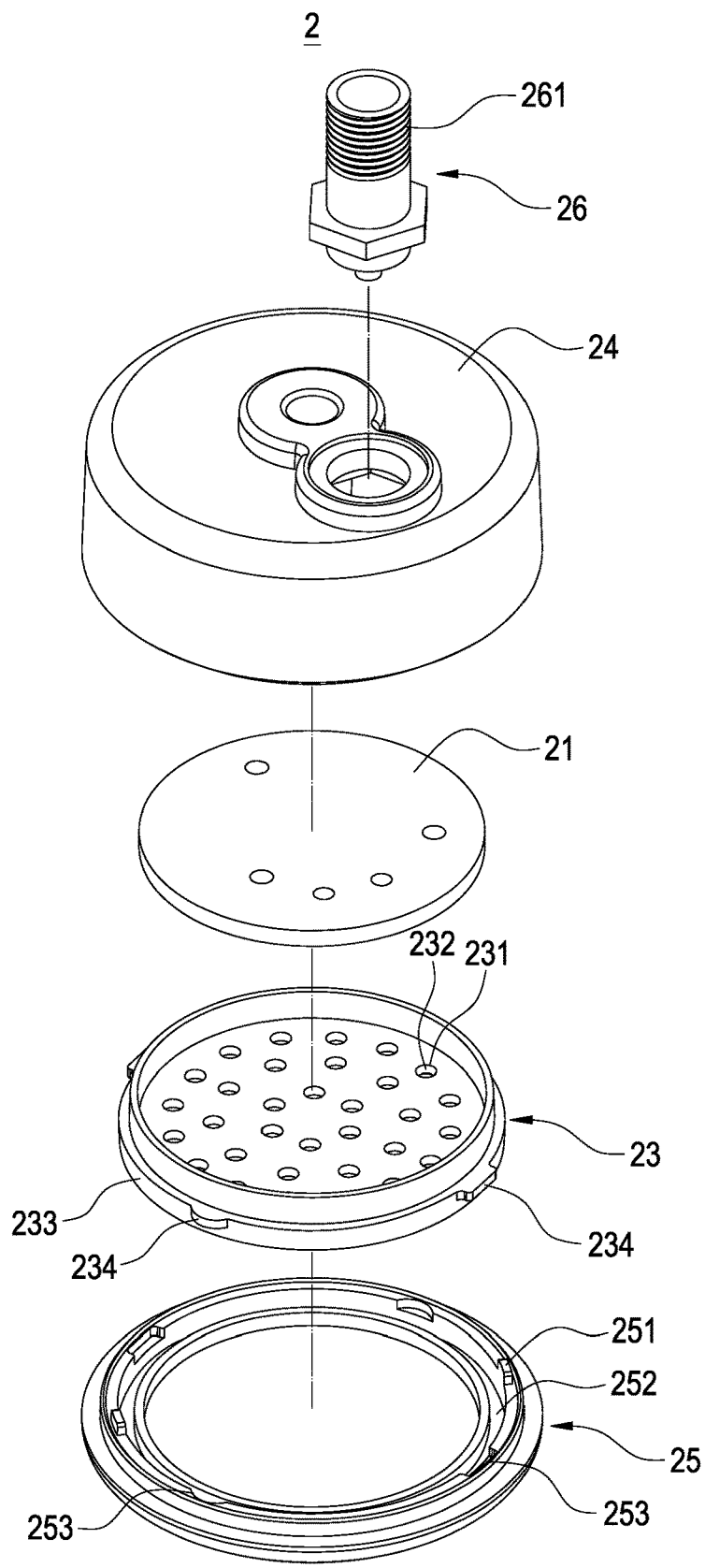
FIG. 1 is an exploded view of the light therapy module of the disclosure.
Figure 2:
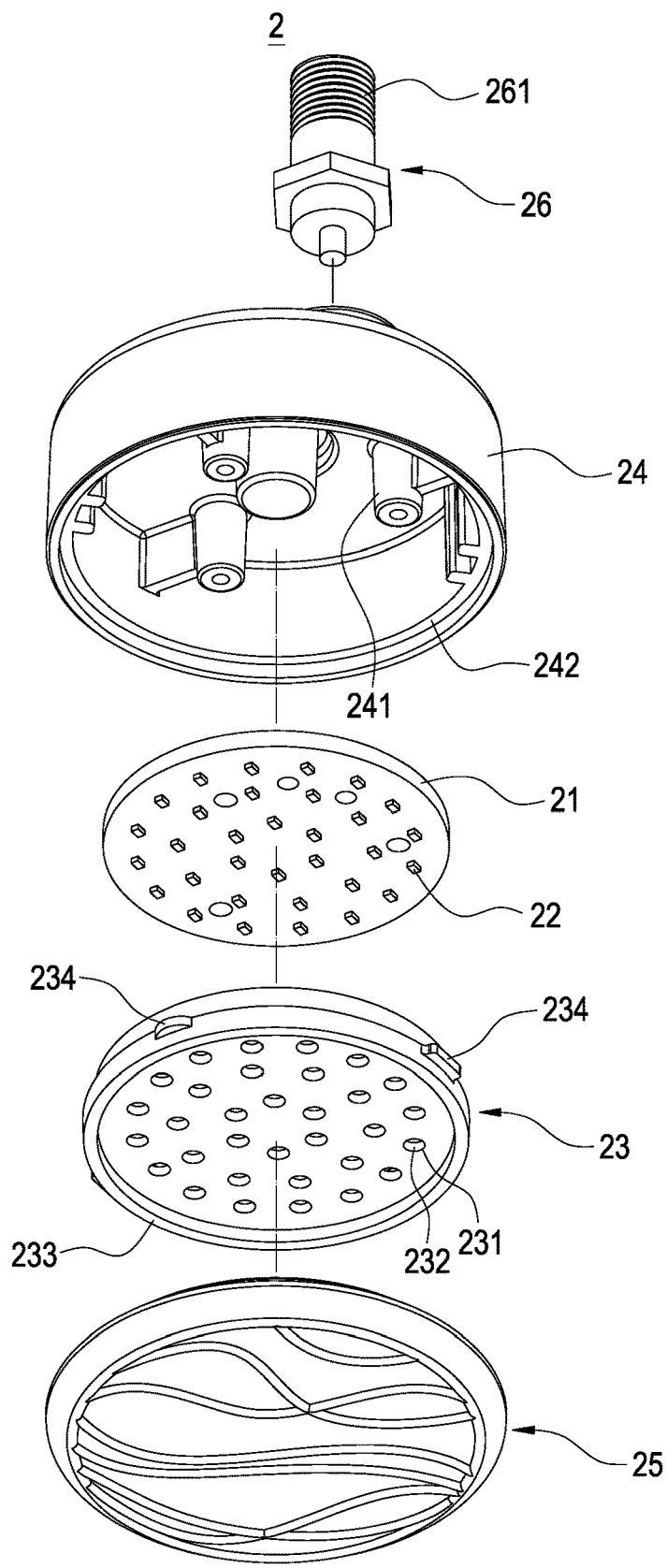
FIG. 2 is another exploded view of the light therapy module of the disclosure.
Figure 3:
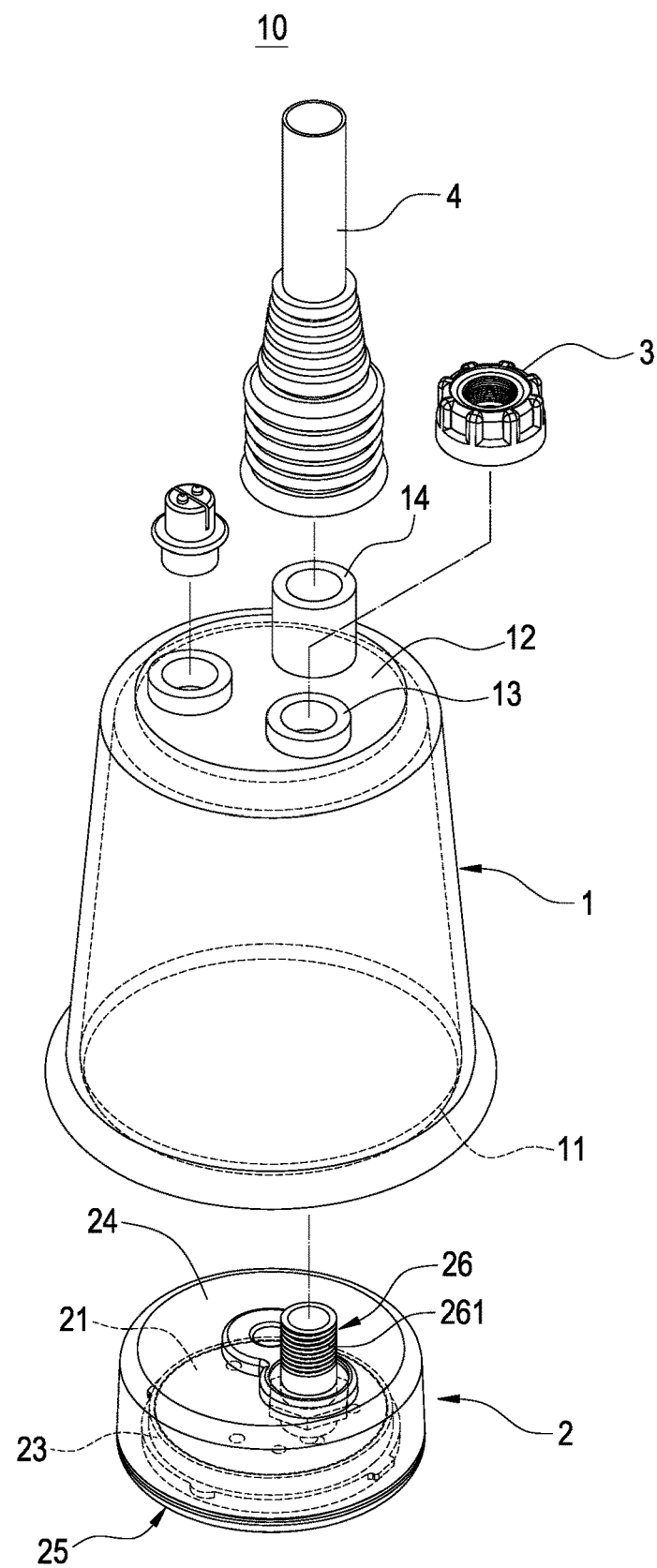
FIG. 3 is an exploded view of the negative-pressure cup structure of the disclosure.
Figure 4:
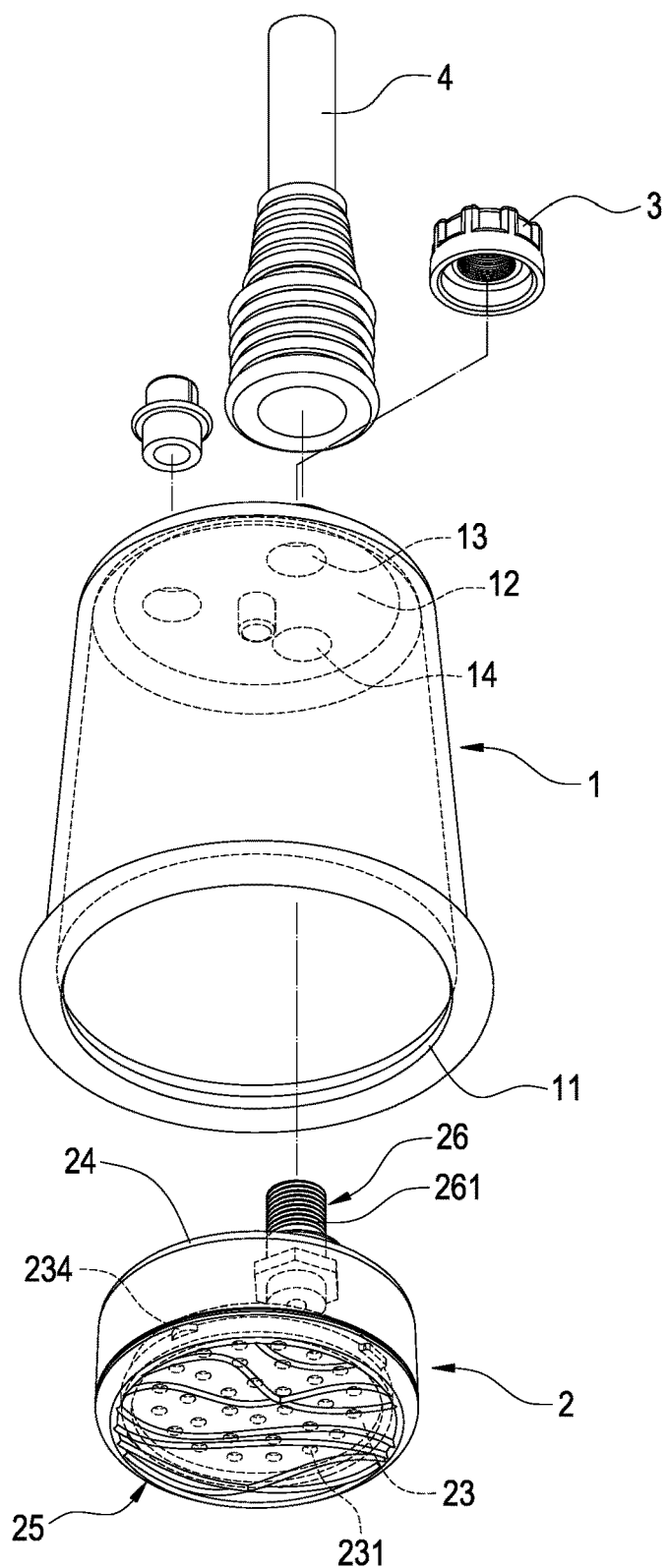
FIG. 4 is another exploded view of the negative-pressure cup structure of the disclosure.
Figure 5:
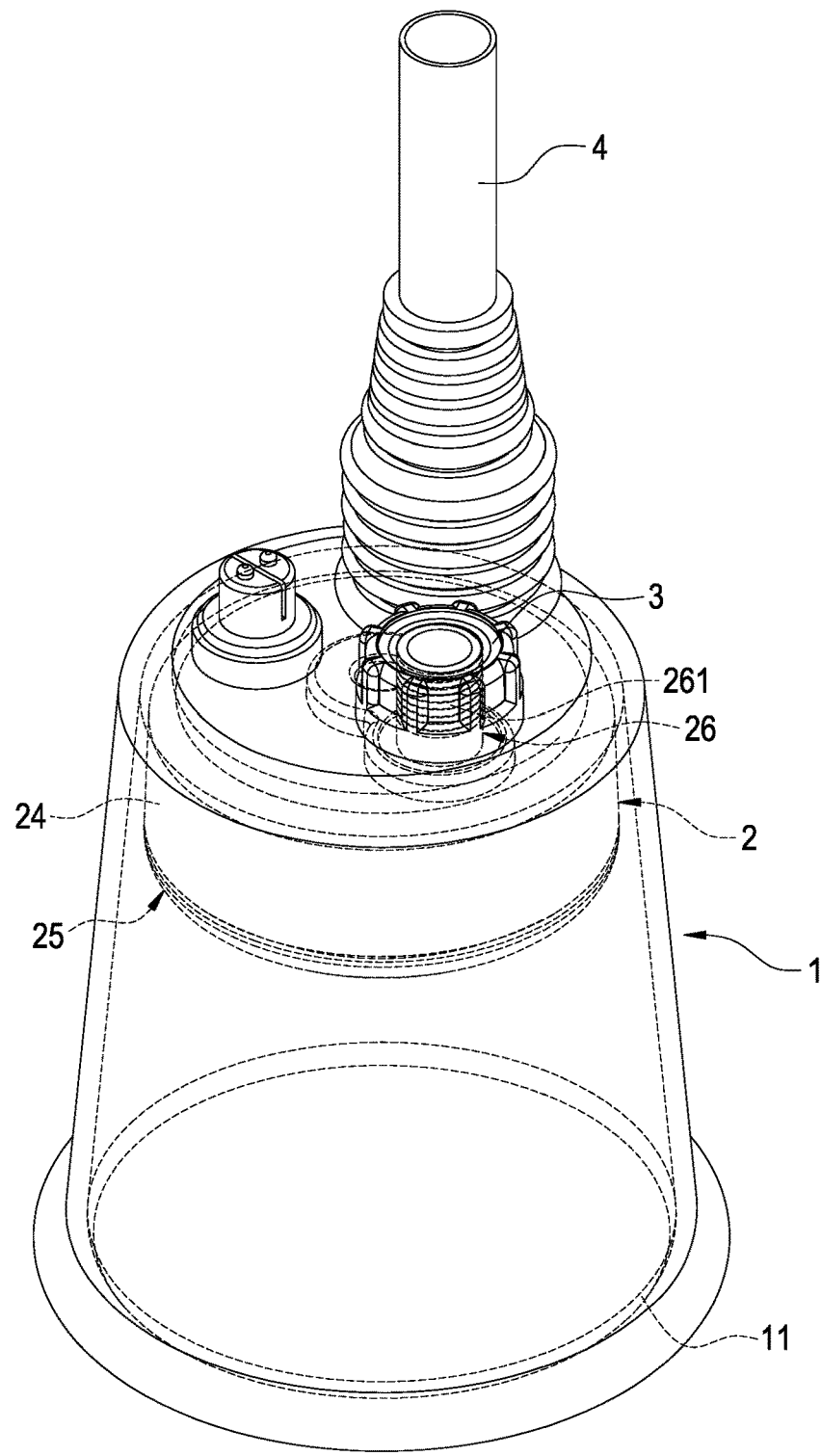
FIG. 5 is an assembled view of the negative-pressure cup structure of the disclosure.
Figure 6:
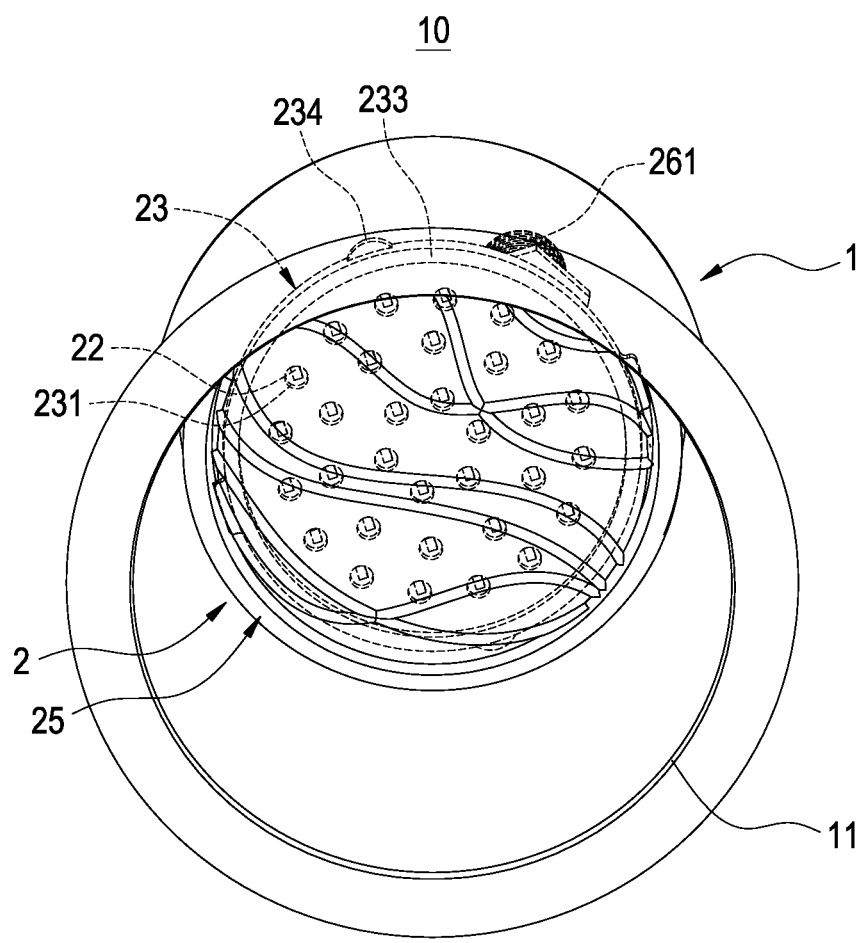
FIG. 6 is a top view of the negative-pressure cup structure of the disclosure.

The technical contents of this disclosure will become apparent with the detailed description of embodiments accompanied with the illustration of related drawings as follows. It is intended that the embodiments and drawings disclosed herein are to be considered illustrative rather than restrictive.

Please refer to FIGS. 1-8. The disclosure provides a negative-pressure cup structure with a light therapy module. The negative-pressure cup structure 10 includes a negative-pressure cup body 1 and a light therapy module 2.

As shown in FIGS. 3-8, the negative-pressure cup body 1 has a rim 11 and a bottom 12 on an end opposite to the rim 11. The bottom 12 is provided with a fixing hole 13 and one or more vents 14. The negative-pressure cup body 1 is made of a transparent material such as, but not limited to, transparent plastic or glass.

As shown in FIGS. 1-8, the light therapy module 2 is received in the negative-pressure cup body 1 and includes a circuit board 21, multiple light-emitting diodes (LEDs) 22 mounted on the circuit board 21 and irradiating corresponding to the rim 11, and a condenser 23 arranged corresponding to the LEDs 22. The condenser 23 is provided with multiple via holes 231 and multiple reflecting annular walls 232 respectively formed in the multiple via holes 231. Each LED 22 is arranged corresponding to each via hole 231.

The LEDs 22 has at least two colors. For example, the LEDs 22 may be LEDs with RGB three colors, which can provide light output with different colors by adjusting the illuminous power of red LEDs, green LEDs and blue LEDs to bring different effects of light therapy.

In addition, the condenser 23 may be made of a metal material with a reflective surface to make inner walls of the via holes 231 form the reflecting annular walls 232. Alternatively, each reflecting annular wall 232 is formed by coating the inner wall of each via hole 231 with a reflective material.

In detail, the light therapy module 2 further includes a lamp shade 24 and a lamp cover 25 assembled to each other. The circuit board 21 and the condenser 23 are received in the lamp shade 24. The lamp cover 25 covers the LEDs 22 and the condenser 23.

In addition, the lamp shade 24 is extended with multiple fixing rods 241 supporting on the circuit board 21 and an annular block 242 stopped and positioned on the condenser 23. An inner periphery of the lamp shade 24 is provided with multiple engaging troughs 243. The lamp cover 25 is extended with multiple latches 251 engaging with each engaging trough 243 to make the lamp cover 25 firmly assembled with the lamp shade 24. The circuit board 21 may be fixed to the fixing rods 241 by fastening, but not limited to this.

Furthermore, the lamp cover 25 is formed with an annular groove 252 and multiple notches 253. An outer periphery of the condenser 23 is downward extended with an annular flange 233 engaging with the annular groove 252 and outward extended with multiple protrusions 234 engaging with each notch 253 to make the condenser 23 firmly assembled with the lamp cover 25. The lamp cover 25 is made of a transparent material such as, but not limited to, transparent plastic or glass.

Also, the light therapy module 2 further includes a power connector 26. One end of the power connector 26 is fixed to the lamp shade 24 and electrically connected to the circuit board 21, and the other end of the power connector 26 has a threaded rod 261 passing the fixing hole 13. The power connector 26 is used for supplying electricity to the circuit board 21 and the LEDs 22. The power connector 26 is fixed to the circuit board 21 by, but not limited to, soldering.

As shown in FIGS. 3-5 and 7, the negative-pressure cup structure 10 of the disclosure further includes a nut 3. The threaded rod 261 of the power connector 26 is screwed with the nut 3 to make the power connector 26 firmly assembled with the negative-pressure cup body 1.

As shown in FIGS. 3-5 and 7-8, the negative-pressure cup structure 10 of the disclosure further includes a suction pump 4 fixed to and communicating with the vent 14. When the negative-pressure cup structure 10 is being used, the rim 11 of the negative-pressure cup body 1 is used to attach on human body's skin, the suction pump 4 sucks air from the inside of the negative-pressure cup body 1 through the vent 14 to form negative pressure in the negative-pressure cup body 1 to further make the negative-pressure cup body 1 adhere to a human body's surface.

Figure 7:
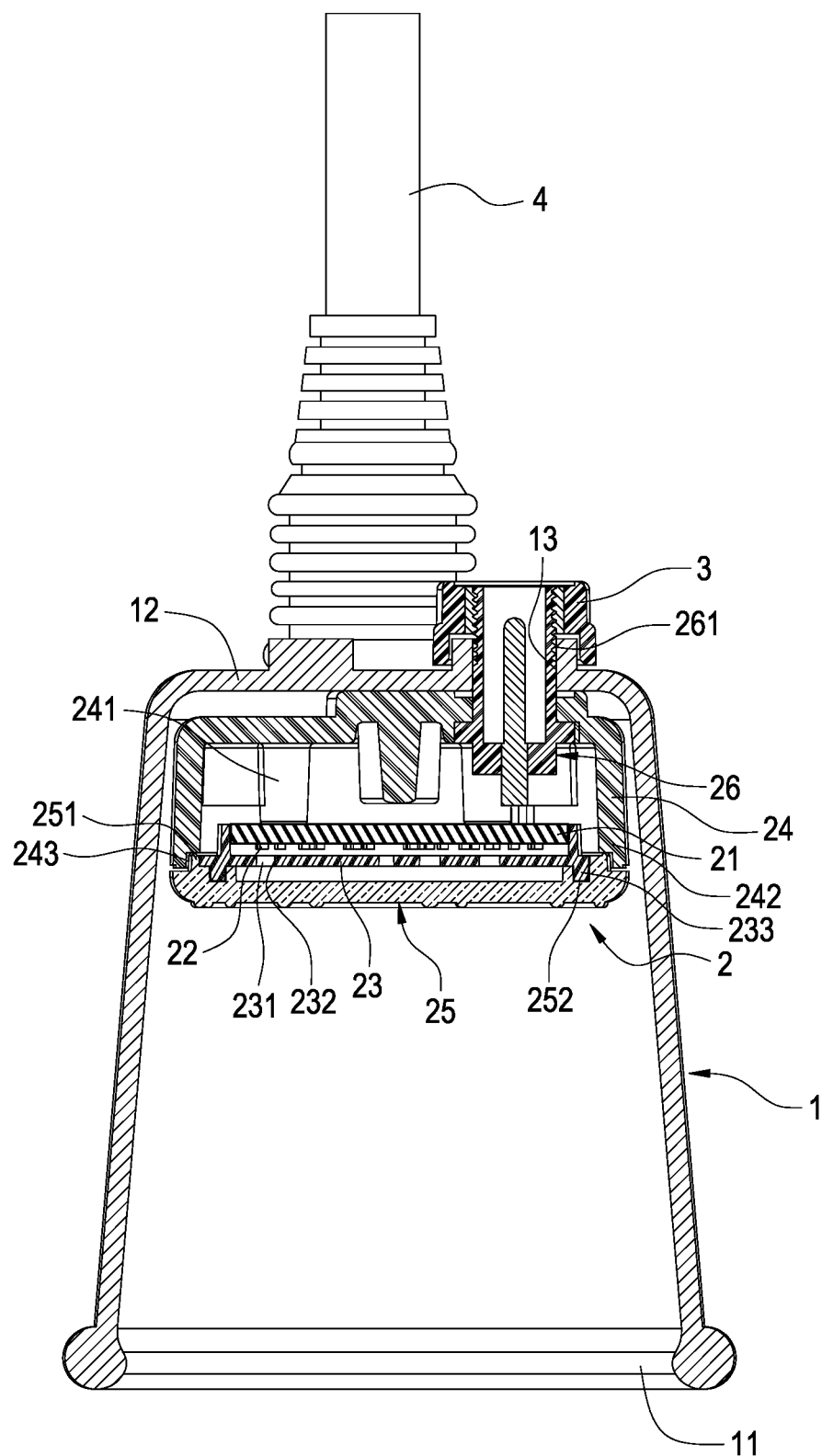
FIG. 7 is a cross-sectional view of the negative-pressure cup structure of the disclosure.
Figure 8:
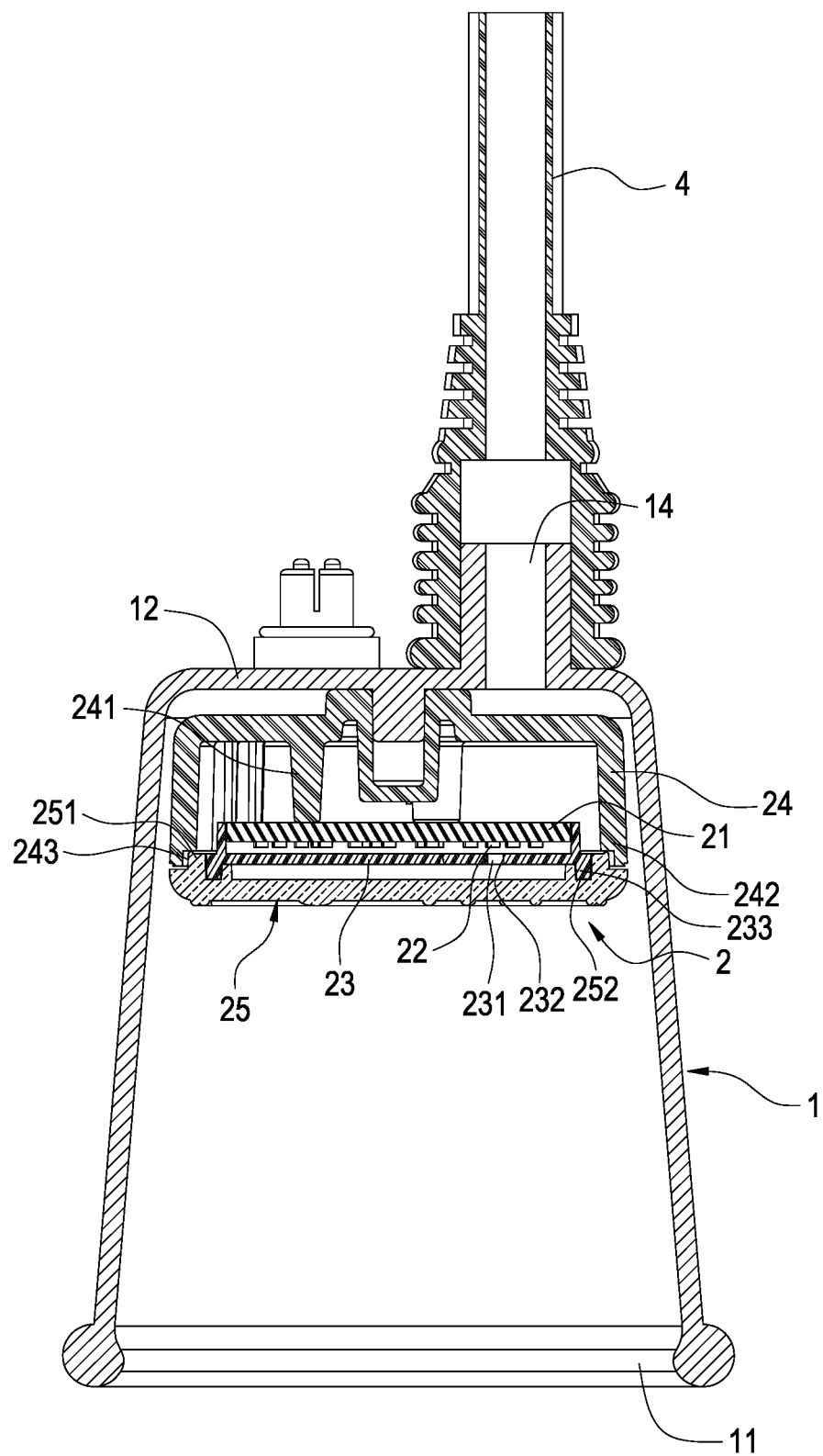
FIG. 8 is a cross-sectional view of the negative-pressure cup structure of the disclosure.

As shown in FIGS. 7-8, the negative-pressure cup structure 10 of the disclosure utilizes the light therapy module 2 to be received in the negative-pressure cup body 1 and the light therapy module 2 may provide output with different colors and wavelengths to make the skin negative-pressure cupping range be the light irradiating range as well. The negative-pressure cup structure 10 not only adheres to a surface of human body to generate effects of stimulating skin, relaxing muscle or implementing breast enhancement, but also adds the effects of light therapy and skin care.

In addition, each LED 22 is arranged corresponding to the reflecting annular wall 232 of each via hole 231 and the reflecting annular wall 232 possesses a desirable effect of reflection so as to make the lights from the LEDs 22 be concentrated to irradiate out from the via holes 231. The light scattering may be avoided and the efficiency of light therapy of the negative-pressure cup structure may be enhanced.

Figure 9:
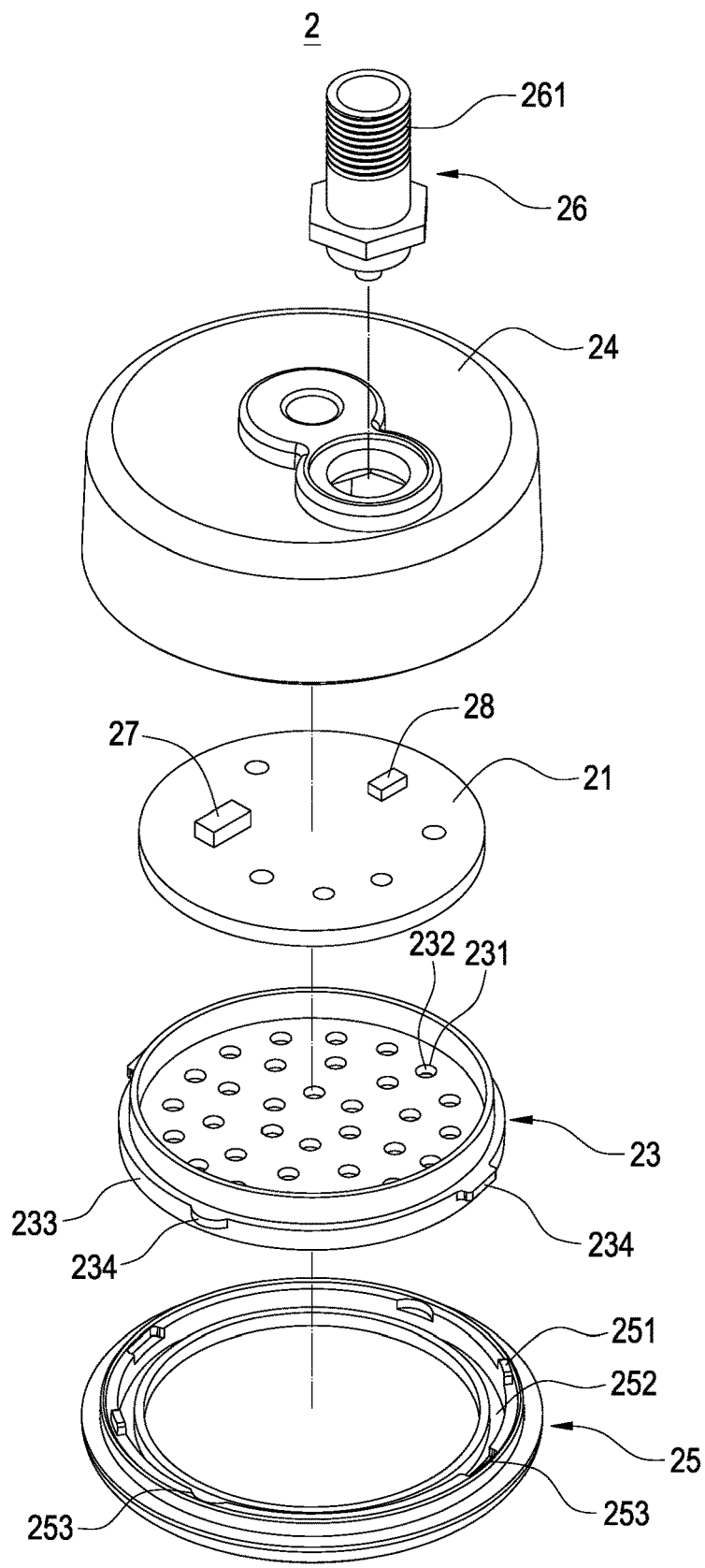
FIG. 9 is an exploded view of another embodiment of the light therapy module of the disclosure.

Please refer to FIG. 9, which shows another embodiment of the light therapy module 2 of the disclosure. The embodiment of FIG. 9 is similar to the embodiment of FIGS. 1-8. The embodiment of FIG. 9 differs from the embodiment of FIGS. 1-8 by the light therapy 2 further including a quartz oscillator 27 and a current fuse 28 installed on the circuit board 21.

In detail, the quartz oscillator 27 is used to assist the circuit board 21 for determining the total time (or the interval time) when the LEDs 22 are flickering more accurate. The current fuse 28 is used to cut off the power when overcurrent occurs to prevent the electronic components on the circuit board 21 from being broken or to avoid overlong irradiating time of the LEDs 22 to make the negative-pressure cup structure 10 have desirable using convenience and service life.

While this disclosure has been described by means of specific embodiments, numerous modifications and variations could be made thereto by those skilled in the art without departing from the scope and spirit of this disclosure set forth in the claims.

What is claimed is:

1. A negative-pressure cup structure comprising:
    a negative-pressure cup body, comprising a rim; and
    a light therapy module, received in the negative-pressure cup body, comprising a circuit board and multiple light-emitting diodes (LEDs) mounted on the circuit board and irradiating in the direction of the rim;
    wherein the light therapy module further comprises a condenser arranged corresponding to the LEDs, the condenser comprises multiple via holes and multiple reflecting annular walls respectively disposed in the multiple via holes, and each LED is arranged corresponding to each via hole;
    wherein the light therapy module further comprises a lamp shade and a lamp cover assembled with each other, the circuit board and the condenser are received in the lamp shade, and the lamp cover covers the LEDs and the condenser;
    wherein the lamp shade comprises multiple fixing rods extended therefrom to support the circuit board and an annular block configured to be stopped and positioned on the condenser.

2. The negative-pressure cup structure of claim 1, wherein the lamp shade comprises multiple engaging troughs disposed on an inner periphery thereof, and the lamp cover comprises multiple latches extended therefrom and engaged with the multiple engaging troughs respectively.

3. The negative-pressure cup structure of claim 1, wherein the light therapy module further comprises a quartz oscillator and a current fuse, the quartz oscillator and the current fuse are installed on the circuit board.

4. The negative-pressure cup structure of claim 1, wherein the LEDs comprise at least two different colors.

5. The negative-pressure cup structure of claim 1, further comprising a nut, wherein the negative-pressure cup body comprises a fixing hole, the light therapy module further comprises a power connector, one end of the power connector is fixed to the lamp shade and electrically connected to the circuit board, and the power connector comprises a threaded rod disposed on another end thereof, the threaded rod passes through the fixing hole and is screwed with the nut.

6. The negative-pressure cup structure of claim 5, wherein the power connector is fixed to the circuit board in a manner of soldering.

7. The negative-pressure cup structure of claim 5, further comprising: a suction pump, wherein the negative-pressure cup body comprises a bottom on an end opposite to the rim, the negative-pressure cup body comprises the fixing hole and at least one vent disposed on the bottom, and the suction pump is fixed to and communicates with the at least one vent.

8. A negative-pressure cup structure comprising:
    a negative-pressure cup body, comprising a rim; and
    a light therapy module, received in the negative-pressure cup body, comprising a circuit board and multiple light-emitting diodes (LEDs) mounted on the circuit board and irradiating in the direction of the rim;
    wherein the light therapy module further comprises a condenser arranged corresponding to the LEDs, the condenser comprises multiple via holes and multiple reflecting annular walls respectively disposed in the multiple via holes, and each LED is arranged corresponding to each via hole;

wherein the light therapy module further comprises a lamp shade and a lamp cover assembled with each other, the circuit board and the condenser are received in the lamp shade, and the lamp cover covers the LEDs and the condenser;

wherein the lamp cover comprises an annular groove and multiple notches, the condenser comprises an annular flange extended downward from an outer periphery thereof to engage with the annular groove and multiple protrusions extended outward from the outer periphery thereof to engage with the multiple notches respectively.

9. The negative-pressure cup structure of claim 8, further comprising a nut, wherein the negative-pressure cup body comprises a fixing hole, the light therapy module further comprises a power connector, one end of the power connector is fixed to the lamp shade and electrically connected to the circuit board, and the power connector comprises a threaded rod disposed on another end thereof, the threaded rod passes through the fixing hole and is screwed with the nut.

10. The negative-pressure cup structure of claim 9, wherein the power connector is fixed to the circuit board in a manner of soldering.

11. The negative-pressure cup structure of claim 9, further comprising: a suction pump, wherein the negative-pressure cup body comprises a bottom on an end opposite to the rim, the negative-pressure cup body comprises the fixing hole and at least one vent disposed on the bottom, and the suction pump is fixed to and communicates with the at least one vent.

12. The negative-pressure cup structure of claim 8, wherein the lamp shade comprises multiple engaging troughs disposed on an inner periphery thereof, and the lamp cover comprises multiple latches extended therefrom and engaged with the multiple engaging troughs respectively.

13. The negative-pressure cup structure of claim 8, wherein the light therapy module further comprises a quartz oscillator and a current fuse, the quartz oscillator and the current fuse are installed on the circuit board.

14. The negative-pressure cup structure of claim 8, wherein the LEDs comprise at least two different colors.

* * * * *